US00RE45723E

(19) United States
(12) Reissued Patent
Shimose et al.

(10) Patent Number: US RE45,723 E
(45) Date of Reissued Patent: Oct. 6, 2015

(54) PROCESS FOR PRODUCING AMINO ACIDS

(71) Applicant: Kyowa Hakko Bio Co., Ltd., Chiyoda-ku, Tokyo (JP)

(72) Inventors: Tsuyoshi Shimose, Toyonaka (JP); Ryou Ohashi, Hofu (JP); Katsumi Fujinaga, Hofu (JP)

(73) Assignee: KYOWA HAKKO BIO CO., LTD., Tokyo (JP)

(21) Appl. No.: 14/329,255

(22) Filed: Jul. 11, 2014

Related U.S. Patent Documents

Reissue of:
(64) Patent No.: 7,888,078
Issued: Feb. 15, 2011
Appl. No.: 11/908,048
PCT Filed: Apr. 12, 2006
PCT No.: PCT/JP2006/307725
§ 371 (c)(1),
(2) Date: Sep. 7, 2007
PCT Pub. No.: WO2006/109830
PCT Pub. Date: Oct. 19, 2006

(30) Foreign Application Priority Data

Apr. 12, 2005 (JP) ..... 2005-114254

(51) Int. Cl.
*C12P 13/22* (2006.01)
*C12P 13/04* (2006.01)
*C12P 13/06* (2006.01)
*C12P 13/14* (2006.01)
*C12P 13/08* (2006.01)

(52) U.S. Cl.
CPC ..... *C12P 13/04* (2013.01); *C12P 13/22* (2013.01); *C12P 13/06* (2013.01); *C12P 13/08* (2013.01); *C12P 13/14* (2013.01)

(58) Field of Classification Search
CPC ..... C12P 13/04
See application file for complete search history.

(56) References Cited

U.S. PATENT DOCUMENTS

| | | | | |
|---|---|---|---|---|
| 4,444,885 | A | 4/1984 | Nakanishi et al. | |
| 5,518,904 | A | 5/1996 | Igarashi et al. | |
| 6,280,980 | B1 * | 8/2001 | Waller | 435/109 |
| 6,962,805 | B2 | 11/2005 | Asakura et al. | |
| 7,127,913 | B2 * | 10/2006 | Witkamp et al. | 62/532 |
| 7,294,491 | B2 * | 11/2007 | Ueda et al. | 435/110 |
| 7,319,025 | B2 * | 1/2008 | Ueda et al. | 435/110 |
| 7,354,744 | B2 * | 4/2008 | Takahashi et al. | 435/110 |
| 2003/0190713 | A1 | 10/2003 | Ueda et al. | |
| 2005/0176115 | A1 * | 8/2005 | Kobayashi et al. | 435/113 |

FOREIGN PATENT DOCUMENTS

| | | |
|---|---|---|
| AU | 80303/91 | 1/1993 |
| AU | 639809 | 1/1993 |
| EP | 0 931 833 | 7/1999 |
| EP | 1 233 068 | 8/2002 |
| EP | 1 233 069 | 8/2002 |
| EP | 1 655 374 | 5/2006 |
| JP | 47-22274 | 6/1972 |
| JP | 53-75387 | 7/1978 |
| JP | 57-41912 | 9/1982 |
| JP | 62-000288 | 1/1987 |
| JP | 62-288 | 1/1987 |
| JP | 62-288 A | 1/1987 |
| JP | 62-265254 | 11/1987 |
| JP | 03-147794 | 6/1991 |
| JP | 03-147794 A | 6/1991 |
| JP | 03-216195 | 9/1991 |
| JP | 5-1717 | 1/1993 |
| JP | 5-304971 | 11/1993 |
| JP | 6-59228 | 8/1994 |
| JP | 07-039385 | 2/1995 |
| JP | 7-121228 | 12/1995 |
| JP | 2958789 | 7/1999 |
| JP | 2958789 B | 7/1999 |
| JP | 3074781 | 6/2000 |
| JP | 3239905 | 10/2001 |
| JP | 2002-238593 | 8/2002 |
| JP | 2004-313202 | 11/2004 |
| JP | 2005-040739 | 2/2005 |
| JP | 4066543 | 1/2008 |
| WO | 2006/109830 | 10/2006 |

OTHER PUBLICATIONS

Amend, et al., "Solubilities of the Common L-α-amino acids as a function of temperature and solution pH", Pure & Appl. Chem., vol. 69, No. 5 (1997) 935-42.
Black, et al., "Crystallisation of Amino Acid", Journal of Crystal Growth, vol. 90 (1988) 136-44.
Doki, et al., "Size Distribution of Needle-Shape Crystals of Monosodium L-Glutamate Obtained by Seeded Batch Cooling Crystallization", Journal of Chemical Engineering of Japan, vol. 37, No. 3 (2004) 436-42.
Doki, Separation Techniques, vol. 31, No. 6 (2001) (Translation).
Ikeda, "Amino Acid Production Processes", Advances in Biochemical Engineering/Biotechnology, vol. 79 (2003) 1-34.
Kubota, et al., "Seeding Effect on Product Crystal Size in Batch Crystallization", Journal of Chemical Engineering of Japan, vol. 35, No. 11 (2002) 1063-71.

(Continued)

*Primary Examiner* — Bruce Campell
(74) *Attorney, Agent, or Firm* — Fitzpatrick, Cella, Harper & Scinto

(57) ABSTRACT

The present invention provides: a process for producing an amino acid which comprises adding crystals of the amino acid having an average particle size of 1 to 120 μm to a medium so that the concentration of the crystals of the amino acid becomes 0.5 g/l or more, culturing a microorganism having the ability to produce the amino acid in the medium, allowing crystals of the amino acid to form and accumulate in the medium, and recovering the crystals of the amino acid from the culture; and a process for producing an amino acid which comprises adding crystals of the amino acid to a medium so that the total surface area of the crystals of the amino acid in the medium becomes 0.02 $m^2/l$, culturing a microorganism having the ability to produce the amino acid in the medium, allowing crystals of the amino acid to form and accumulate in the medium, and recovering the crystals of the amino acid from the culture.

12 Claims, 1 Drawing Sheet

(56) References Cited

OTHER PUBLICATIONS

Lung-Somarriba et al., "Effect of seeded surface area on crystal size distribution in glycine batch cooling crystallization: a seeding methodology", Journal of Crystal Growth, vol. 270 (2004) 624-32.
Crystallization, Mullin, 4th edition (2001) 392-93.
Kagakudaiziten 7, Kagakudaizitenhensyuiinnkai (Feb. 15, 1987) 532.
Kagakudaiziten 9, Kagakudaizitenhensyuiinnkai (Feb. 15, 1987) 216.
The Japanese Biochemical Society, Ed., "Laboratory Course in Biochemistry 11 Amino Acid Metabolism and Biogenic Amine" (1977) 1101-12 (Partial translation), of record.
Ajinomoto Co., Ltd. , "Amino Acid Handbook" (2002) (English Tanslation).
CRC Handbook of Chemistry and Physics , "CRC Handbook of Chemistry and Physics 76th Edition" (1995) 7-1.
Declaration of Noriaki Kubota.
Declaration of Takuji Ueda.
Doki, et al., "Controlling Crystal Grain Size by Batch Crystallization" The Society of Separation Process Engineers, vol. 31, No. 6 (2001) 36-41 (English Tanslation).
Doki, et al., "Reliable and Selective Crystallization of the Metastable a Form Glycine by Seeding", Crystal Growth & Design, vol. 4, No. 1 (2004) 103-107.
Horiba Scientific, "Guidebook to Particle Size Analysis" Horiba Instruments, Inc. (2012) 1-29.
Rawle, et al., "Basic Principles of Particle Size Analysis", 1-8.
Yoshida, "Cultivation Engineering", Biotechnology Textbook Series 13 (1998) 1-8 (English Tanslation).
"Separation Process Engineers (Bunri-Gijutsu)", vol. 31, No. 6 (2001) 36-41.
The Japanese Biochemical Society, Ed., "Laboratory Course in Biochemistry 11 (Seikagaku Jikken Koza 11), Amino Acid Metabolism and Biogenic Amine (Last Part)", (1977) 1101-38.

* cited by examiner

| | ① | ② | ③ | ④ | Control |
|---|---|---|---|---|---|
| Particle size of crystals added ($\mu$m) | 30 | 45 | 70 | 110 | — |
| Addition amount (g/l) | 5.5 | 5.5 | 5.5 | 5.5 | — |
| Photograph of crystals added | | | | | — |
| Specific surface area of crystals added ($m^2/cm^3$) | 0.24 | 0.16 | 0.10 | 0.07 | — |
| Total surface area of crystals added ($m^2/L$) | 0.86 | 0.57 | 0.36 | 0.25 | — |
| Photograph of culture after the completion of culturing | | | | | |
| Recovery rate of crystals (%) | 92.1 | 92.6 | 87.1 | 82.1 | 33.4 |
| Dry content (%) | 98.6 | 98.3 | 96.3 | 96.5 | 83.9 |
| Dry cell amount (%) | 1.5 | 1.1 | 2.5 | 2.2 | 10.7 |

PROCESS FOR PRODUCING AMINO ACIDS

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

TECHNICAL FIELD

The present invention relates to a process for producing amino acids.

BACKGROUND ART

A well-known method for producing amino acids is the fermentation method using microorganisms belonging to the genera Corynebacterium, Brevibacterium, Escherichia, Microbacterium, Serratia, Bacillus and Pseudomonas, and the like (non-patent publication No. 1).

With regard to the above fermentation method, various techniques have been developed for raising the production efficiency. One of these techniques is a process in which crystallization of L-amino acid in a culture is induced by adjusting the temperature and pH of a culture medium or by adding a surfactant to the culture to maintain the L-amino acid concentration in the culture below a certain level, whereby production inhibition by accumulation of L-amino acid at a high concentration can be avoided (patent publication No. 1).

Also known are a process for crystallizing L-glutamic acid (L-Glu) having a relatively low solubility in a culture medium by using a medium adjusted to pH suitable for deposition of L-Glu (patent publication No. 2) and a process for depositing α crystals of L-phenylalanine (L-Phe) in a culture by adding α crystals of L-Phe to the culture or changing the pH of the culture to a value of 7.8 to 8.3 at the stage where the L-Phe concentration in the culture is beyond the saturation solubility (patent publication No. 3).

However, as the culture contains microcrystals of amino acid in the above processes, direct separation of crystals and microbial cells based on the difference in particle size can give only a low yield of amino acid. In order to raise the yield of amino acid in these processes, it is necessary to dissolve crystals of amino acid accumulated in the culture, for example, by addition of water to the culture or heating of the culture, and after microbial cells are separated from the culture by using a centrifugal or filtration separator or the like, crystallization by concentration should be carried out.

As the method for directly separating crystals of amino acid and microbial cells, a method using a liquid cyclone is known (patent publication No. 4). However, the recovery rate of crystals of amino acid by this method does not reach 80%.

As described above, a process for producing an amino acid by fermentation in which the amino acid is crystallized in a medium during the culturing is excellent, but a more efficient process is still needed.

Non-Patent Publication No. 1:
Amino Acid Fermentation, Gakkai Shuppan Center (1986)

Patent Publication No. 1:
Japanese Published Unexamined Patent Application No. 288/87

Patent Publication No. 2:
Japanese Published Unexamined Patent Application No. 238593/02

Patent Publication No. 3:
Japanese Patent No. 3239905

Patent Publication No. 4:
Japanese Patent No. 2958789

DISCLOSURE OF THE INVENTION

Problems to be Solved by the Invention

An object of the present invention is to provide a simple process for producing an amino acid with a high production efficiency.

Means for Solving the Problems

The present invention relates to the following (1) to (7).

(1) A process for producing an amino acid which comprises adding crystals of the amino acid having an average particle size of 1 to 120 μm to a medium so that the concentration of the crystals of the amino acid becomes 0.5 g/l or more, culturing a microorganism having the ability to produce the amino acid in the medium, allowing crystals of the amino acid to form and accumulate in the medium, and recovering the crystals of the amino acid from the culture.

(2) A process for producing an amino acid which comprises adding crystals of the amino acid to a medium so that the total surface area of the crystals of the amino acid in the medium becomes 0.02 $m^2/l$, culturing a microorganism having the ability to produce the amino acid in the medium, allowing crystals of the amino acid to form and accumulate in the medium, and recovering the crystals of the amino acid from the culture.

(3) The process according to the above (1) or (2), wherein the crystals of the amino acid added are those having a specific surface area of 0.06 $m^2/cm^3$ or more.

(4) The process according to any one of the above (1) to (3), wherein the crystals of the amino acid formed and accumulated have an average particle size of 15 μm or more.

(5) The process according to any one of the above (1) to (4), wherein the recovery of the amino acid from the culture is carried out by separating the microorganism producing the amino acid and the accumulated crystals of the amino acid based on the difference in particle size between them.

(6) The process according to any one of the above (1) to (4), wherein the recovery of the amino acid from the culture is carried out by separating the microorganism producing the amino acid and the accumulated crystals of the amino acid based on the difference in specific gravity between them.

(7) The process according to any one of the above (1) to (6), wherein the amino acid is L-glutamine, L-valine, L-leucine, L-isoleucine, L-phenylalanine, L-tyrosine or L-tryptophan.

Effect of the Invention

The present invention provides a simple process for producing an amino acid with a high production efficiency.

BRIEF DESCRIPTION OF THE DRAWINGS

FIG. 1 shows the relationship between the average particle size, specific surface area and total surface area of the crystals of the amino acid added and the form and recovery rate of the crystals of the amino acid accumulated in the medium. In the photographs shown in the FIGURE, the vertical side represents 1000 μm.

BEST MODES FOR CARRYING OUT THE INVENTION

1. Microorganisms Used in the Production Process of the Present Invention

The microorganisms used in the production process of the present invention are not specifically limited so long as they are microorganisms having the ability to produce an amino acid, and they may be microorganisms isolated from nature or microorganisms having artificially enhanced amino acid productivity.

The microorganisms having artificially enhanced amino acid productivity include microorganisms obtained by using the following methods alone or in combination:

(a) a method in which at least one of the mechanisms regulating the biosynthesis of an amino acid is partially released or completely released;

(b) a method in which the expression of at least one of the enzymes involved in the biosynthesis of an amino acid is enhanced;

(c) a method in which the copy number of at least one of the enzyme genes involved in the biosynthesis of an amino acid is increased;

(d) a method in which at least one of the metabolic pathways branching from the biosynthetic pathway of an amino acid into metabolites other than the amino acid is weakened or blocked; and (e) a method in which a cell strain having a higher resistance to an analogue of an amino acid as compared with a wild-type strain is selected.

The methods of the above (a) to (e) are specifically described in the following literature: (a), Agric. Biol. Chem., 43, 105-111 (1979), J. Bacteriol., 110, 761-763 (1972), Appl. Microbiol. Biotechnol., 39, 318-323 (1993), etc.; (b), Agric. Biol. Chem., 43, 105-111 (1979), J. Bacteriol., 110, 761-763 (1972), etc.; (c), Appl. Microbiol. Biotechnol., 39, 318-323 (1993), Agric. Biol. Chem., 39, 371-377 (1987), etc.; (d), Appl. Environ. Microbiol., 38, 181-190 (1979), Agric. Biol. Chem., 42, 1773-1778 (1978), etc.; and (e), Agric. Biol. Chem., 36, 1675-1684 (1972), Agric. Biol. Chem., 41, 109-116 (1977), Agric. Biol. Chem., 37, 2013-2023 (1973), Agric. Biol. Chem., 51, 2089-2094 (1987), etc.

As to the methods for preparing microorganisms having the ability to form and accumulate an amino acid by using the above (a) to (e) singly or in combination, many examples are described in Biotechnology 2nd ed., Vol. 6, Products of Primary Metabolism (VCH Verlagsgesellschaft mbH, Weinheim, 1996) section 14a, 14b; Advances in Biochemical Engineering/Biotechnology 79, 1-35 (2003); and Hiroshi Soda, et al., Amino Acid Fermentation, Gakkai Shuppan Center (1986). In addition, there are a number of reports on the specific methods for preparing microorganisms having the ability to form and accumulate an amino acid; for example, Japanese Published Unexamined Patent Application No. 164297/03; Agric. Biol. Chem., 39, 153-160 (1975); Agric. Biol. Chem., 39, 1149-1153 (1975); Japanese Published Unexamined Patent Application No. 13599/83; J. Gen. Appl. Microbiol., 4, 272-283 (1958); Japanese Published Unexamined Patent Application No. 94985/88; Agric. Biol. Chem., 37, 2013-2023 (1973); WO97/15673; Japanese Published Unexamined Patent Application No. 18596/81; Japanese Published Unexamined Patent Application No. 144092/81; and PCT National Publication No. 511086/03. By referring to the above literature and the like, the microorganisms having the ability to produce an amino acid can be prepared.

The above microorganisms having the ability to produce an amino acid may be any microorganisms to which the above methods (a) to (e) can be applied or any microorganisms having the above genetic characters. Preferred are procaryotes and more preferred are bacteria.

Examples of procaryotes include microorganisms belonging to the genera Escherichia, Serratia, Bacillus, Brevibacterium, Corynebacterium, Microbacterium, Pseudomonas, Agrobacterium, Alicyclobacillus, Anabaena, Anacystis, Arthrobacter, Azotobacter, Chromatium, Erwinia, Methylobacterium, Phormidium, Rhodobacter, Rhodopseudomonas, Rhodospirillum, Scenedesmus, Streptomyces, Synechoccus and Zymomonas. Specific examples are Escherichia coli, Bacillus subtilis, Bacillus megaterium, Bacillus amyloliquefaciens, Bacillus coagulans, Bacillus licheniformis, Bacillus pumilus, Brevibacterium ammoniagenes, Brevibacterium immariophilum, Brevibacterium saccharolyticum, Brevibacterium flavum, Brevibacterium lactofermentum, Corynebacterium glutamicum, Corynebacterium acetoacidophilum, Microbacterium ammoniaphilum, Serratia ficaria, Serratia fonticola, Serratia liquefaciens, Serratia marcescens, Pseudomonas aeruginosa, Pseudomonas putida, Agrobacterium radiobacter, Agrobacterium rhizogenes, Agrobacterium rubi, Anabaena cylindrica, Anabaena doliolum, Anabaena flosaquae, Arthrobacter aurescens, Arthrobacter citreus, Arthrobacter globiformis, Arthrobacter hydrocarboglutamicus, Arthrobacter mysorens, Arthrobacter nicotianae, Arthrobacter paraffineus, Arthrobacter protophormiae, Arthrobacter roseoparaffinus, Arthrobacter sulfureus, Arthrobacter ureafaciens, Chromatium buderi, Chromatium tepidum, Chromatium vinosum, Chromatium warmingii, Chromatium fluviatile, Erwinia uredovora, Erwinia carotovora, Erwinia ananas, Erwinia herbicola, Erwinia punctata, Erwinia terreus, Methylobacterium rhodesianum, Methylobacterium extorquens, Phormidium sp. ATCC 29409, Rhodobacter capsulatus, Rhodobacter sphaeroides, Rhodopseudomonas blastica, Rhodopseudomonas marina, Rhodopseudomonas palustris, Rhodospirillum rubrum, Rhodospirillum salexigens, Rhodospirillum salinarum, Streptomyces ambofaciens, Streptomyces aureofaciens, Streptomyces aureus, Streptomyces fungicidicus, Streptomyces griseochromogenes, Streptomyces griseus, Streptomyces lividans, Streptomyces olivogriseus, Streptomyces rameus, Streptomyces tanashiensis, Streptomyces vinaceus and Zymomonas mobilis. Preferred procaryotes include bacteria belonging to the genera Escherichia, Serratia, Bacillus, Brevibacterium, Corynebacterium, Pseudomonas and Streptomyces, for example, the above-mentioned species belonging to the genera Escherichia, Serratia, Bacillus, Brevibacterium, Corynebacterium, Pseudomonas and Streptomyces. More preferred bacteria include Escherichia coli, Corynebacterium glutamicum, Corynebacterium ammoniagenes, Corynebacterium lactofermentum, Corynebacterium flavum, Corynebacterium efficasis, Brevibacterium flavum, Brevibacterium lactofermentum, Bacillus subtilis, Bacillus megaterium, Serratia marcescens, Pseudomonas putida, Pseudomonas aeruginosa, Streptomyces coelicolor and Streptomyces lividans. Particularly preferred are Escherichia coli, Corynebacterium glutamicum and Brevibacterium ammoniagenes. More specific examples include FERM P-4806, ATCC 14751 and ATCC 14752 strains having the ability to produce L-glutamine, ATCC 13005 and ATCC 19561 strains having the ability to produce L-valine, FERM BP-4704 and ATCC 21302 strains having the ability to produce L-leucine, FERM BP-3757 and ATCC 14310 strains having the ability to produce L-isoleucine, ATCC 13281 and MCC 21669 strains having the ability to produce L-phenylalanine, ATCC 21652 strain having the ability to produce L-tyrosine, and DSM 10118, DSM 10121, DSM 10123 and FERM BP-1777 strains having the ability to produce L-tryptophan.

The above strains designated by FERM Nos., ATCC Nos. and DSM Nos. are available from International Patent Organism Depositary, National Institute of Advanced Industrial Science and Technology (Japan), American Type Culture Collection (U.S.A.) and Deutsche Sammlung von Mikroorganismen and Zellkulturen (Germany), respectively.

2. Process for Producing an Amino Acid of the Present Invention

The processes for producing amino acids of the present invention include: (1) a process for producing an amino acid which comprises adding crystals of the amino acid having an average particle size of 1 to 120 μm to a medium so that the concentration of the crystals of the amino acid becomes 0.5 g/l or more, culturing the microorganism having the ability to produce the amino acid of the above 1 in the medium, allowing crystals of the amino acid to form and accumulate in the medium, and recovering the crystals of the amino acid from the culture; and (2) a process for producing an amino acid which comprises adding crystals of the amino acid to a medium so that the total surface area of the crystals of the amino acid in the medium becomes 0.02 $m^2$/l or more, culturing the microorganism having the ability to produce the amino acid of the above 1 in the medium, allowing crystals of the amino acid to form and accumulate in the medium, and recovering the crystals of the amino acid from the culture.

Culturing of the microorganism in the above medium can be carried out in the same manner as the conventional method used for culturing a microorganism, except for the addition of crystals of an amino acid.

That is, any of natural media and synthetic media can be used insofar as it is a medium suitable for efficient culturing of the microorganism which contains carbon sources, nitrogen sources, inorganic salts, etc. which can be assimilated by the microorganism, preferably a liquid medium.

As the carbon sources, any carbon sources that can be assimilated by the microorganism can be used. Examples of suitable carbon sources include carbohydrates such as glucose, fructose, sucrose, molasses containing them, starch and starch hydrolyzate; organic acids such as acetic acid and propionic acid; and alcohols such as ethanol and propanol.

As the nitrogen sources, ammonia, ammonium salts of organic or inorganic acids such as ammonium chloride, ammonium sulfate, ammonium acetate and ammonium phosphate, and other nitrogen-containing compounds can be used as well as peptone, meat extract, yeast extract, corn steep liquor, casein hydrolyzate, soybean cake, soybean cake hydrolyzate, and various fermented microbial cells and digested products thereof.

Examples of the inorganic salts include potassium dihydrogenphosphate, dipotassium hydrogenphosphate, magnesium phosphate, magnesium sulfate, sodium chloride, ferrous sulfate, manganese sulfate, copper sulfate and calcium carbonate.

As to the crystals of an amino acid to be added in the above process (1), there is no restriction on the average particle size, the amount, the kind of amino acid, the kind of crystal form, etc. of the crystals so far as they are crystals of an amino acid having an average particle size of 1 to 120 μm which can give a medium having a crystal concentration of 0.5 g/l or more. The average particle size of the crystals of an amino acid to be added is 1 to 120 μm, preferably 2 to 110 μm, more preferably 5 to 70 μm, further preferably 7 to 50 μm, particularly preferably 10 to 35 μm, and most preferably 11 to 13 μm.

The amount of the crystals of an amino acid is such that the concentration of the crystals of the amino acid in the medium after the addition thereof becomes 0.5 g/l or more, preferably 2 to 30 g/l, more preferably 3 to 25 g/l, further preferably 4 to 22 g/l, particularly preferably 5 to 20 g/l, and most preferably 5.5 to 16.5 g/l.

As to the combination of the above average particle size of the crystals of an amino acid to be added and addition amount thereof, there is no restriction so far as it is a combination of an average particle size of 1 to 120 μm and an amount giving a medium having a crystal concentration of 0.5 g/l or more. That is, the combination is an average particle size of 1 to 120 μm and an amount giving a medium having a crystal concentration of 0.5 g/l or more, preferably an average particle size of 2 to 110 μm and an amount giving a medium having a crystal concentration of 2 to 30 g/l, more preferably an average particle size of 5 to 70 μm and an amount giving a medium having a crystal concentration of 3 to 25 g/l, further preferably an average particle size of 7 to 50 μm and an amount giving a medium having a crystal concentration of 4 to 22 g/l, particularly preferably an average particle size of 10 to 35 μm and an amount giving a medium having a crystal concentration of 5 to 20 g/l, and most preferably an average particle size of 11 to 13 μm and an amount giving a medium having a crystal concentration of 5.5 to 16.5 g/l.

The crystals of an amino acid may be added to the medium before inoculating the microorganism having the ability to produce the amino acid or may be added at any time during the culturing period after inoculation of the microorganism having the ability to produce the amino acid. The crystals are added preferably at some time after the microorganism having the ability to produce the amino acid is inoculated in the medium, between around the time when the amino acid concentration in the medium reaches the saturation solubility and the time when crystals of the amino acid deposit in the medium, more preferably at some time after the amino acid concentration in the medium reached the saturation solubility and before crystals of the amino acid deposit in the medium, further preferably at some time when the medium is supersaturated with the amino acid and before crystals of the amino acid deposit in the medium. In the above, "before crystals of the amino acid deposit in the medium" refers preferably to the period during which the presence of amino acid crystals is not observed at all in the medium; however, deposition of a slight amount of amino acid crystals is allowable insofar as the effect of the present invention can be achieved in respect of the crystal recovery rate and the like.

When the crystals of an amino acid are added to a medium supersaturated with the amino acid, the amount of the crystals to be added is 0.5 g/l or more, preferably 2 to 30 g/l, more preferably 3 to 25 g/l, further preferably 4 to 22 g/l, particularly preferably 5 to 20 g/l, most preferably 5.5 to 16.5 g/l based on the amount of the medium at the time of addition.

When the crystals of an amino acid are added to a medium supersaturated with the amino acid, the combination of the average particle size of the crystals of an amino acid to be added and addition amount thereof are as follows: the combination is an average particle size of 1 to 120 μm and an amount of 0.5 g/l or more based on the amount of the medium at the time of addition, preferably an average particle size of 2 to 110 μm and an amount of 2 to 30 g/l, more preferably an average particle size of 5 to 70 μm and an amount of 3 to 25 g/l, further preferably an average particle size of 7 to 50 μm and an amount of 4 to 22 g/l, particularly preferably an average particle size of 10 to 35 μm and an amount of 5 to 20 g/l, and most preferably an average particle size of 11 to 13 μm and an amount of 5.5 to 16.5 g/l.

As to the crystals of an amino acid to be added in the above process (2), there is no restriction on the average particle size, the amount, the kind of amino acid, the kind of crystal form, etc. of the crystals so far as the total surface area of the crystals of the amino acid in the medium becomes 0.02 $m^2/l$ or more. The crystals to be added are crystals such that the total surface area of the crystals in the medium after addition becomes 0.02 $m^2/l$ or more, preferably 0.08 to 70 $m^2/l$, more preferably 0.2 to 23 $m^2/l$, further preferably 0.4 to 15 $m^2/l$, particularly preferably 0.7 to 9.3 $m^2/l$, most preferably 2.0 to 7.0 $m^2/l$.

Specifically, examples of the crystals of an amino acid to be added in the above process (2) include crystals having an average particle size of 1 to 120 μm and giving a medium having a crystal concentration of 0.5 g/l or more, preferably having an average particle size of 2 to 110 μm and giving a medium having a crystal concentration of 2 to 30 g/l, more preferably having an average particle size of 5 to 70 μm and giving a medium having a crystal concentration of 3 to 25 g/l, further preferably having an average particle size of 7 to 50 μm and giving a medium having a crystal concentration of 4 to 22 g/l, particularly preferably having an average particle size of 10 to 35 μm and giving a medium having a crystal concentration of 5 to 20 g/l, and most preferably having an average particle size of 11 to 13 μm and giving a medium having a crystal concentration of 5.5 to 16.5 g/l.

The time for addition of the crystals of an amino acid to the medium is the same as in the above process (1).

When the crystals of an amino acid are added to a medium supersaturated with the amino acid, the crystals of the amino acid to be added are crystals such that the total surface area of the crystals calculated based on the amount of the medium at the time of addition is 0.02 $m^2/l$ or more, preferably 0.08 to 70 $m^2/l$, more preferably 0.2 to 23 $m^2/l$, further preferably 0.4 to 15 $m^2/l$, particularly preferably 0.7 to 9.3 $m^2/l$, most preferably 2.0 to 7.0 $m^2/l$.

Specifically, examples of the crystals of an amino acid include crystals having an average particle size of 1 to 120 μm whose amount based on the amount of the medium at the time of addition is 0.5 g/l or more, preferably crystals having an average particle size of 2 to 110 μm whose amount based on the amount of the medium at the time of addition is 2 to 30 g/l, more preferably crystals having an average particle size of 5 to 70 μm whose amount based on the amount of the medium at the time of addition is 3 to 25 g/l, further preferably crystals having an average particle size of 7 to 50 μm whose amount based on the amount of the medium at the time of addition is 4 to 22 g/l, particularly preferably crystals having an average particle size of 10 to 35 μm whose amount based on the amount of the medium at the time of addition is 5 to 20 g/l, and most preferably crystals having an average particle size of 11 to 13 μm whose amount based on the amount of the medium at the time of addition is 5.5 to 16.5 g/l.

In the above, the amount of the medium in the culture may be measured by any known method. For example, the amount of the medium can be measured by separating the medium and insoluble matters such as microbial cells by centrifuging the culture, measuring the volume of the sedimented insoluble matters, and then subtracting the measured volume from the amount of the culture.

Further, the crystals of an amino acid to be added in the above processes (1) and (2) include crystals having an average specific surface area of 0.06 $m^2/cm^3$ or more, preferably 0.07 to 7.2 $m^2/cm^3$, more preferably 0.07 to 1.43 $m^2/cm^3$, further preferably 0.1 to 1.0 $m^2/cm^3$, particularly preferably 0.14 to 0.72 $m^2/cm^3$.

The amino acid to be added in the above processes (1) and (2) may be any amino acid that can be produced by a microorganism, but is preferably an amino acid selected from the group consisting of L-glutamine, L-valine, L-leucine, L-isoleucine, L-phenylalanine, L-tyrosine and L-tryptophan, more preferably an amino acid selected from the group consisting of L-glutamine, L-valine and L-leucine, further preferably L-glutamine. However, α crystals of L-phenylalanine may be excluded from the crystals of an amino acid to be added in the process of the present invention.

The crystals of an amino acid to be added to a medium in the present invention can be obtained as commercially available products or by using known methods such as the fermentation method and purification method. The crystals can also be obtained by preparing crystals of an amino acid having a desired average particle size by crushing commercially available amino acid crystals or amino acid crystals obtained by the above known methods by using commercially available mills, e.g., M4 Jiyu Mill (Nara Machinery Co., Ltd.), Atomizer TAP-20 (Tokyo Atomizer Mfg. Co., Ltd.) and Air Classifying Mill (Hosokawa Micron Powder Systems).

For example, crystals of an amino acid having an average particle size of about 45 μm can be obtained by crushing crystals of an amino acid having an average particle size of about 110 μm which are obtained by a known fermentation method and purification method using M4 Jiyu Mill under the following conditions: screen, Φ 1.0 mm; rotation, 4500 rpm; speed, ca. 400 kG/h. Further, crystals of an amino acid having an average particle size of about 11 μm can be obtained by crushing the crystals obtained by the above crushing treatment under the following conditions: screen, Φ 0.3 mm; rotation, 6000 rpm; speed, ca. 200 kG/h.

The specific surface area of crystals of an amino acid can be measured by using commercially available analyzers, e.g., SK LASER MICRON SIZER LMS-24 (particle distribution analyzer by the laser diffraction and scattering method, produced by Seishin Enterprise Co., Ltd.). In the measurement of the specific surface area of crystals of an amino acid, it is preferable to calculate the specific surface area assuming that the crystals are spherical and are similar in shape.

The total surface area of crystals of an amino acid can be calculated from the specific surface area of the crystals and the addition amount thereof.

Culturing is usually carried out under aerobic conditions, for example, by shaking culture or submerged spinner culture under aeration. The culturing temperature is preferably 15 to 40° C., and the culturing period is usually 5 hours to 7 days. The pH is maintained at 3.0 to 9.0 during the culturing. The pH adjustment is carried out by using an organic or inorganic acid, an alkali solution, urea, calcium carbonate, ammonia, etc.

If necessary, antibiotics such as ampicillin and tetracycline may be added to the medium during the culturing.

When a microorganism transformed with an expression vector comprising an inducible promoter is cultured, an inducer may be added to the medium, if necessary. For example, in the case of a microorganism transformed with an expression vector comprising lac promoter, isopropyl-β-D-thiogalactopyranoside or the like may be added to the medium; and in the case of a microorganism transformed with an expression vector comprising trp promoter, indoleacrylic acid or the like may be added.

The amino acid accumulated in the medium in the above processes may be any amino acid that can be produced by a microorganism, and is preferably an amino acid selected from the group consisting of L-glutamine, L-valine, L-leucine, L-isoleucine, L-phenylalanine, L-tyrosine and L-tryptophan, more preferably an amino acid selected from the group consisting of L-glutamine, L-valine and L-leucine, further preferably L-glutamine.

The crystals of an amino acid accumulated in the medium in the above processes include crystals having an average particle size of 15 μm or more, preferably 20 μm or more, more preferably 30 μm or more, further preferably 40 μm or more, particularly preferably 50 μm or more, most preferably 60 μm or more.

In the processes of the present invention, recovery of the crystals of an amino acid in the culture can be carried out by any ordinary method for purification of amino acids. Preferably, the crystals of an amino acid are separated and purified by directly separating the crystals and the microbial cells in the culture after the completion of culturing by utilizing the difference in particle size and specific gravity between them.

The above separation and purification of crystals of an amino acid utilizing the difference in particle size and specific gravity can be carried out by known methods such as the gravitational classification method and the centrifugal classification method. Preferred is the centrifugal classification method, particularly, the one using a decanter-type centrifuge.

By the recovery methods described above, sufficiently purified crystals of an amino acid can be obtained with a high recovery rate. If necessary, the crystals can be further purified by ordinary methods using active carbon, ion-exchange resins, etc. or by means such as extraction with an organic solvent, crystallization, thin layer chromatography and high performance liquid chromatography.

Certain embodiments of the present invention are illustrated in the following examples. These examples are not to be construed as limiting the scope of the present invention.

EXAMPLE 1

Production of Crystals of L-Glutamine (1)

Corynebacterium glutamicum ATCC 14752 was cultured in a production medium (250 g/l glucose, 30 g/l $NH_4Cl$, 1.0 g/l $K_2HPO_4$, 1.0 g/l $KH_2PO_4$, 0.5 g/l $MgSO_4.7H_2O$, 20 mg/l $FeSO_4$, 2 mg/l $MnSO_4.4H_2O$, 10 μg/l biotin and 1 mg/l thiamine hydrochloride, pH 6.8) in a 500-l jar fermenter with appropriate adjustment of pH and temperature. After the start of culturing, at a time after the L-glutamine concentration in the medium reached the saturation solubility and before crystals of L-glutamine deposited in the medium, crystals of L-glutamine having an average particle size of 40 μm were added to the medium so that the crystal concentration became 16.5 g/l. Then, the culturing was continued, thus growing crystals of L-glutamine in the medium. The culturing was terminated about 96 hours after the start thereof, whereby 210 l of a culture containing 90 g/l L-glutamine was obtained. Crystals of L-glutamine (6.2 kg) were obtained from the culture by separation using a decanter (PTM006, Tomoe Engineering Co., Ltd.). The average particle size of the obtained crystals was 62 μm. The recovery rate of the crystals deposited in the medium by use of the decanter was 98.9%.

EXAMPLE 2

Production of Crystals of L-Glutamine (2)

Culturing was carried out in the same manner as in Example 1, except that crystals of L-glutamine having the average particle size shown in FIG. 1 were used as the crystals to be added to the medium, and crystals of L-glutamine were obtained. The specific surface area of crystals of L-glutamine was measured using SK LASER MICRON SIZER LMS-24 (particle distribution analyzer by the laser diffraction and scattering method, produced by Seishin Enterprise Co., Ltd.). In the measurement of the specific surface area of crystals of L-glutamine, the calculation was made assuming that the crystals are spherical and are similar in shape.

FIG. 1 shows the form of the crystals of L-glutamine added and the crystals of L-glutamine obtained by fermentation, and the recovery rate, dry content, etc. of the crystals of L-glutamine.

It can be seen from FIG. 1 that when the crystals were not added to the medium, the recovery rate of crystals by centrifugation was lowered due to deposition of microcrystals in the medium, and that addition of crystals having a smaller particle size tends to increase the recovery rate of crystals. In the cases where the crystals were added, the amino acid crystals obtained in the medium at the completion of culturing had an average particle size of 30 μm or more. Further, it was found that the content of the crystals obtained by separating the produced crystals using a decanter and then drying the separated crystals by dehydration using a basket-type centrifuge (dry content) was improved by adding crystals having a larger total surface area.

The above results have revealed that according to the process of the present invention, in fermentative production of various amino acids including L-glutamine, the particle size of crystals of an amino acid deposited in the medium during the culturing can be controlled by adding crystals of the amino acid to the medium to keep the degree of supersaturation of the amino acid in the medium below a certain level and to allow an appropriate number of crystals of the amino acid to be present in the medium as seed crystals, that is, by adjusting the average particle size and the amount or the total surface area of the crystals of the amino acid to be added to the medium, and as a result, crystals of the amino acid which are easily separable from microbial cells can be obtained with a high recovery rate.

INDUSTRIAL APPLICABILITY

According to the present invention, amino acids can be efficiently produced in a simple manner.

The invention claimed is:

1. A process for producing an amino acid, which comprises:

*culturing a microorganism having an ability to produce the amino acid in a medium,* adding crystals of the amino acid having an average particle size of [1 to 120] *7 to 50* μm to [a] *the* medium *at some time after the amino acid concentration in the medium reaches the saturation solubility and before crystals of the amino acid deposit in the medium* so that the concentration of the crystals of the amino acid becomes 0.5 g/l or more, culturing [a] *the* microorganism having the ability to produce the amino acid in the medium, allowing *the* crystals of the amino acid to [form] *grow to crystals of the amino acid having an average particle size of 30 μm or more* and accumulate in the medium, and recovering the crystals of the amino acid from the culture by separating the microorganism producing the amino acid and the accumulated crystals of the amino acid based on the difference in particle size or specific gravity between them.

2. A process for producing an amino acid, which comprises:

*culturing a microorganism having an ability to produce the amino acid in a medium,* adding crystals of the amino acid *having an average particle size of 7 to 50 μm* to [a] *the* medium *at some time after the amino acid concentration in the medium reaches the saturation solubility and before crystals of the amino acid deposit in the medium* so that the total surface area of the crystals of the amino acid in the medium becomes 0.02 $m^2/l$ *or more*, culturing [a] *the* microorganism having the ability to produce the amino acid in the medium, allowing *the* crystals of the amino acid to [form] *grow to crystals of the amino acid having an average particle size of 30 μm or more* and accumulate in the medium, and recovering the crystals of the amino acid from the culture by separating the microorganism producing the amino acid and the accumulated crystals of the amino acid based on the difference in particle size or specific gravity between them.

3. The process according to claim 1 or 2, wherein the crystals of the amino acid added are those having a specific surface area of 0.06 $m^2/cm^3$ or more.

[4. The process according to claim 3, wherein the crystals of the amino acid formed and accumulated have an average particle size of 15 μm or more.]

5. The process according to claim 3, wherein the amino acid is L-glutamine, L-valine, L-leucine, L-isoleucine, L-phenylalanine, L-tyrosine or L-tryptophan.

[6. The process according to claim 4, wherein the amino acid is L-glutamine, L-valine, L-leucine, L-isoleucine, L-phenylalanine, L-tyrosine or L-tryptophan.]

7. The process according to claim 1, wherein the amino acid is L-glutamine, L-valine, L-leucine, L-isoleucine, L-phenylalanine, L-tyrosine or L-tryptophan.

8. The process according to claim 2, wherein the amino acid is L-glutamine, L-valine, L-leucine, L-isoleucine, L-phenylalanine, L-tyrosine or L-tryptophan.

[9. The process according to claim 4, wherein the crystals of the amino acid formed and accumulated have an average particle size of 20 μm or more.]

[10. The process according to claim 9, wherein the crystals of the amino acid formed and accumulated have an average particle size of 30 μm or more.]

11. The process according to claim [10] *3*, wherein the crystals of the amino acid formed and accumulated have an average particle size of 40 μm or more.

12. The process according to claim 11, wherein the crystals of the amino acid formed and accumulated have an average particle size of 50 μm or more.

13. The process according to claim 12, wherein the crystals of the amino acid formed and accumulated have an average particle size of 60 μm or more.

*14. The process according to claim 11, wherein the amino acid is L-glutamine, L-valine, L-leucine, L-isoleucine, L-phenylalanine, L-tyrosine or L-tryptophan.*

*15. The process according to claim 12, wherein the amino acid is L-glutamine, L-valine, L-leucine, L-isoleucine, L-phenylalanine, L-tyrosine or L-tryptophan.*

*16. The process according to claim 13, wherein the amino acid is L-glutamine, L-valine, L-leucine, L-isoleucine, L-phenylalanine, L-tyrosine or L-tryptophan.*

* * * * *